(12) United States Patent
Nappa et al.

(10) Patent No.: US 6,262,321 B1
(45) Date of Patent: Jul. 17, 2001

(54) CATALYTIC MANUFACTURE OF VINYL FLUORIDE

(75) Inventors: Mario Joseph Nappa, Newark; V. N. Mallikarjuna Rao, Wilmington, both of DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 3 days.

(21) Appl. No.: 09/308,402

(22) PCT Filed: Nov. 10, 1997

(86) PCT No.: PCT/US97/20291

§ 371 Date: May 18, 1999

§ 102(e) Date: May 18, 1999

(87) PCT Pub. No.: WO98/22414

PCT Pub. Date: May 28, 1998

Related U.S. Application Data

(60) Provisional application No. 60/031,092, filed on Nov. 21, 1996.

(51) Int. Cl.[7] .................................................... C07C 17/25
(52) U.S. Cl. ........................................... 570/158; 570/156
(58) Field of Search ..................................... 570/156, 158

(56) References Cited

U.S. PATENT DOCUMENTS

| | | | |
|---|---|---|---|
| 2,478,933 | * | 8/1949 | Bratton et al. ........................ 570/156 |
| 2,599,631 | * | 6/1952 | Harmon ................................ 570/156 |
| 3,607,955 | | 9/1971 | Gardner . |
| 4,978,649 | | 12/1990 | Surovikin et al. . |
| 5,136,113 | | 8/1992 | Rao . |
| 5,396,000 | | 3/1995 | Nappa et al. . |
| 5,559,069 | | 9/1996 | Rao et al. . |
| 5,945,573 | | 8/1999 | Nappa et al. . |
| 6,093,859 | | 7/2000 | Nappa et al. . |

FOREIGN PATENT DOCUMENTS

| | | |
|---|---|---|
| 0 461 297 A1 | 12/1991 | (EP) . |
| 0 644 173 A1 | 3/1995 | (EP) . |
| 0 726 243 A1 | 8/1996 | (EP) . |
| 1 330 146 | 5/1963 | (FR) . |
| 9-67281 | 3/1997 | (JP) . |
| WO 98/33755 | 8/1998 | (WO) . |

OTHER PUBLICATIONS

Abstract No 126:277171w, CA Selects: Organofluorine Chemistry, Issue No. 11, p. 5, 1997.

* cited by examiner

*Primary Examiner*—Alan Siegel

(57) ABSTRACT

This invention relates to a process for the production of vinyl fluoride by dehydrofluorination of 1,1-difluoroethane in the presence of a catalyst containing magnesium and/or zinc.

14 Claims, No Drawings

CATALYTIC MANUFACTURE OF VINYL FLUORIDE

This application is a national filing under 35 USC 371 of International Application No. PCT/US97/20291 filed Nov. 10, 1997 and claims priority of U.S. Provisional Application No. 60/031,092 filed Nov. 21, 1996.

FIELD OF THE INVENTION

This invention relates to processes for the production of vinyl fluoride, and more particularly, to catalysts and to a catalytic process for the dehydrofluorination of 1,1-difluoroethane to vinyl fluoride.

BACKGROUND

Vinyl fluoride is a useful monomer for the preparation of fluorocarbon polymers which have excellent weathering and chemical resistance properties.

Vinyl fluoride can be produced from acetylene and hydrogen fluoride using mercury catalysts. It can also be produced by the dehydrofluorination of 1,1-difluoroethane. The dehydrofluorination of 1,1-difluoroethane to vinyl fluoride and hydrogen fluoride is an equilibrium reaction. According to published literature the following equilibrium concentrations of vinyl fluoride (VF), based on the moles of VF divided by the moles of HFC-152a +VF, have been determined; about 13% VF at 227° C., about 40% VF at 327° C. and about 99% VF at 427° C.

U.S. Pat. No. 2.599,631 discloses a process for the manufacture of vinyl fluoride by the dehydrofluorination of HFC-152a The dehydrofluorination is done in the presence or absence of a catalyst. The dehydrofluorination catalysts disclosed include oxygen, charcoal, and the free metals, salts and oxides of the elements of Groups IA, IB, IIA, IIB, VB and VIII of the periodic table. In an example using the divalent Group II metal compound calcium fluoride as a catalyst (at about 500° C.), the conversion of HFC-1 52a to vinyl fluoride was 66% (i.e., about 66% of equilibrium). There is an ongoing interest in developing more efficient catalysts for the conversion of HFC- 152a to VF.

SUMMARY OF THE INVENTION

A process is provided for the manufacture of vinyl fluoride (i.e., $CH_2$=CHF, VF or 1141) from 1,1-difluoroethane (i.e., $CH_3CHF_2$, F152a or HFC-152a) which comprises contacting said, 1,1-difluoroethane at an elevated temperature with a catalyst containing at least one divalent Group II metal compound. The process of this invention is characterized by contacting said 1,1-difluoroethane at a temperature of from about 200° C. to 400° C. with a catalyst containing (a) at least one compound selected from the oxides, fluorides and oxyfluorides of magnesium, zinc and mixtures of magnesium and zinc, and optionally (b) at least one compound selected from the oxides, fluorides and oxyfluorides of aluminum; provided that the atomic ratio of any metals other than magnesium and zinc (e.g., aluminum) in total, to the total of magnesium and zinc in said catalyst is about 1:4. or less (e.g., 1:9).

DETAILED DISCUSSION

The present invention provides a process for the manufacture of vinyl fluoride by contacting 1,1-difluoroethane in the vapor phase in the presence of catalysts selected from the group consisting of oxides, fluorides and oxyfluorides of magnesium, zinc and mixtures of magnesium and zinc. The catalysts may also contain metals other than magnesium and/or zinc provided that the atomic ratio of metals other than magnesium and zinc to the total of magnesium and zinc is about 1:4, or less. Of note are embodiments which contain in addition to the oxides, fluorides and/or oxyfluorides of magnesium and zinc, at least one compound selected from the oxides, fluorides and oxyfluorides of aluminum; provided that the atomic ratio of aluminum to the total of magnesium and zinc in said catalyst is about 1:4, or less (e.g., about 1:9). Preferred catalysts include catalysts consisting essentially of magnesium fluoride, and catalysts consisting essentially of magnesium fluoride and at least one compound selected from the oxides, fluorides and oxyfluorides of aluminum.

A suitable catalyst may be prepared, for example, as follows:

Magnesium oxide is dried until essentially all water is removed, e.g., for about 18 hours at about 100° C. The dried material is then transferred to the reactor to be used. The temperature is then gradually increased to about 400° C. while maintaining a flow of nitrogen through the reactor to remove any remaining traces of moisture from the magnesium oxide and the reactor. The temperature is then lowered to about 200° C. and a fluoriding agent such as HF or other vaporizable fluorine containing compounds such as $SF_4$, $CCl_3F$, $CCl_2F_2$, $CHF_3$ or $CCl_2FCClF_2$, diluted with nitrogen is passed through the reactor. The nitrogen can be gradually reduced until only HF or other vaporizable fluorine containing compounds is being passed through the reactor. At this point the temperature can be increased to about 450° C. and held at that temperature for a time sufficient (depending on the fluoriding agent flowrate and the catalyst volume) to convert the magnesium oxide to a fluoride content corresponding to at least 40% by weight (e.g., for from 15 to 300 minutes). The fluorides are in the form of magnesium fluoride or magnesium oxyfluoride; the remainder of the catalyst is magnesium oxide. It is understood in the art that fluoriding conditions such as time and temperature can be adjusted to provide higher than 40 weight % fluoride-containing material.

Another suitable procedure for the catalyst preparation is to add ammonium hydroxide to a solution of magnesium nitrate and (if present) zinc nitrate and/or aluminum nitrate. The ammonium hydroxide is added to the nitrate solution to a pH of about 8.8. At the end of the addition, the solution is filtered, the solid obtained is washed with water, dried and slowly heated to 500° C., where it is calcined. The calcined product is then treated with a suitable fluorine-containing compound as described above.

The physical shape of the catalyst is not critical and may, for example, include pellets, powders or granules. Although not necessary, catalysts which have not been fluorided can be treated with HF before use. It is thought that this converts some of the surface oxides to oxyfluorides. This pretreatment can be accomplished by placing the catalyst in a suitable container (which can be the reactor to be used to perform the reaction of the instant invention) and thereafter, passing HF over the dried catalyst so as to partially saturate the catalyst with HF. This is conveniently carried out by passing HF over the catalyst for a period of time (e.g., about 15 to 300 minutes) at a temperature of, for example, about 200° C. to about 450° C. Nevertheless, this HF treatment is not essential.

The reaction temperature will normally be within the range from about 200° C. to about 400° C., preferably about 225° C. to 375° C. To provide for low acetylene by-product formation and to enhance catalyst life, the temperature is preferably kept within the range of from about 250° C. to about 300° C., more preferably, from about 250° C. to about 280° C.

The 1,1-difluoroethane is typically passed over the catalyst at a rate of about 60 volumes to about 3600 volumes per volume of catalyst per hour; preferably 120 volumes to 720 volumes per volume of catalyst per hour. These volumes correspond to a contact time of about 60 seconds to about 1 second and preferably about 30 seconds to about 5 seconds. Normally a contact time is employed which is sufficient to provide a dehydrofluorination of HFC-152a equal to at least 50% of the equilibrium value for conversion of 1,1-difluoroethane to vinyl fluoride at the temperature employed; preferably at least 80%, and more preferably at least 90% of the equilibrium value at a given reaction temperature.

The reaction pressure can be subatmospheric, atmospheric or superatmospheric. Generally, near atmospheric pressures are preferred.

Unreacted starting material can be recycled to the reactor for the production of additional $CH_2=CHF$. Vinyl fluoride (b.p. −72° C.) may be recovered from the reaction product and any unreacted 1,1-difluoroethane (b.p. −25° C.) by conventional procedures such as distillation.

The process of this invention can be carried out readily in the vapor phase using well known chemical engineering practice.

The reaction zone and its associated feed lines, effluent lines and associated units should be constructed of materials resistant to hydrogen fluoride. Typical materials of construction, well-known to the fluorination art, include stainless steels, in particular of the austenitic type, the well-known high nickel alloys, such as Monel® nickel-copper alloys, Hastelloy® nickel-based alloys and, Inconel® nickel-chromium alloys, and copper-clad steel. Silicon carbide is also suitable for reactor fabrication.

Without further elaboration, it is believed that one skilled in the art can, using the description herein, utilize the present invention to its fullest extent. The following specific embodiments are to be construed as illustrative, and not as constraining the remainder of the disclosure in any way whatsoever.

EXAMPLES

| Legend | |
|---|---|
| 1141 is $CH_2=CHF$ | GCMS is gas chromatography- |
| F152a is $CH_3CHF_2$ | mass spectroscopy |
| CT is contact time | $k_f$ is rate constant of the |
| $k_r$ is rate constant of the reverse reaction | forward reaction |

PREPARATION OF CATALYSTS

General Procedure for the Preparation of Metal Fluoride Catalysts:

Unless stated otherwise, the following general procedure was followed for the preparation of metal fluoride catalysts containing one or more metal fluorides. An aqueous solution of the metal(s) halide(s) or nitrate(s) in deionized water was treated with 48% aqueous HF with stirring. Stirring was continued overnight and the slurry evaporated to dryness on a steam bath. The dried solid was then calcined in air at 400° C. for about four hours, cooled to room temperature, crushed and sieved to provide a 12–20 mesh (1.68–0.84 mm) fraction which was used in catalyst evaluations.

Preparation of $MgF_2$ Catalyst:

Following the general procedure described above for the preparation of fluorinated catalysts, a $MgF_2$ catalyst was prepared from 150.0 g of $Mg(NO_3)_2.6H_2O$, 500 mL deionized water and 75 mL 48% aqueous HF.

Preparation of $MgF_2/AlF_3$ (98:2):

Following the general procedure described above for the preparation of fluorinated catalysts, a $MgF_2/AlF_3$ catalyst having a nominal magnesium to aluminum atomic ratio of 43:1 was prepared from 251.28 g $Mg(NO_3)_2.6H_2O$, 7.50 g $Al(NO_3)_3.9H_2O$ and 100 mL 48% aqueous HF.

Preparation of $MgF_2/AlF_3$ (9:1):

Following the general procedure described above for the preparation of fluorinated catalysts, a $MgF_2/AlF_3$ catalyst having a nominal magnesium to aluminum atomic ratio of 9:1 was prepared from 237.6 g $Mg(NO_3)_2.6H_2O$, 34.76 g $Al(NO_3)_3.9H_2O$ and 120 mL 48% aqueous HF.

Preparation of $MgF_2/AlF_3$ (1:1):

Following the general procedure described above for the preparation of fluorinated catalysts, a $MgF_2/AlF_3$ catalyst having a nominal magnesium to aluminum atomic ratio of 1:1.1 was prepared from 128.2 g $Mg(NO_3)_2.6H_2O$, 187.56 g $Al(NO_3)_3.9H_2O$ and 120 mL 48% aqueous HF.

Preparation of $MgF_2/AlF_3$ (1:9):

Following the general procedure described above for the preparation of fluorinated catalysts, a $MgF_2/AlF_3$ catalyst having a nominal magnesium to aluminum atomic ratio of 1:11 was prepared from 23.07 g $Mg(NO_3)_2.6H_2O$, 337.6 g $Al(NO_3)_3.9H_2O$ and 166 ml 48% aqueous HF.

Preparation of $ZnF_2$:

Following the general procedure described for the preparation of fluorinated catalysts, $ZnF_2$ was prepared from an aqueous solution of 148.73 g of $Zn(NO_3)_2.6H_2O$ and 62 mL of 48% aqueous HF.

Preparation of $ZnF_2/AlF_3$ (1:1):

Following the general procedure described for the preparation of fluorinated catalysts, a $ZnF_2/AlF_3$ catalyst having a nominal zinc to aluminum atomic ratio of 2.4:1 was prepared from 148.73 g $Zn(NO_3)_2.6H_2O$, 187.56 g $Al(NO_3)_3.9H_2O$ and 150 mL 48% aqueous HF.

Preparation of $ZnF_2/AlF_3$ (1:9):

Following the general procedure described for the preparation of fluorinated catalysts a $ZnF_2/AlF_3$ catalyst having a nominal zinc to aluminum atomic ratio of 0.2:1 was prepared from 26.77 g $Zn(NO_3)_2.6H_2O$, 337.6 g $Al(NO_3)_3.9H_2O$ and 166 mL 48% aqueous HF.

Preparation of $ZnF_2/AlF_3$ (9:1):

Following the general procedure described for the preparation of fluorinated catalysts, a $ZnF_2/AlF_3$ catalyst having a nominal zinc to aluminum atomic ratio of 24:1 was prepared from 267.71 g $Zn(NO_3)_2.6H_2O$, 33.76 g $Al(NO_3)_3.9H_2O$ and 120 mL 48% aqueous HF.

Preparation of Fluorided Magnesium Oxide

To a reactor was charged 5.42 g, 5 cc of a commercial sample of magnesium oxide which was granulated to 12/20 mesh (1.68/0.84 mm) prior to use. It was heated in a flow of nitrogen (50 cc/min) for about one hour at 175° C. After this period, a flow of HF (50 cc/min) was started through the reactor. The reactor was maintained for an additional hour at 175° C. After this period, the nitrogen flow was reduced to 20 cc/min and the HF flow increased to 80 cc/min. The reactor temperature was then gradually raised to 400° C. over a two hour period. The reactor contents were cooled to room temperature under a flow of nitrogen. When discharged, the fluorinated catalyst weighed 6.6 g which corresponds to a 40% conversion of MgO to $MgF_2$.

Magnesium oxide, gamma-alumina, calcium fluoride and alpha and beta-aluminum fluorides were obtained from commercial sources as powders and were granulated prior to use.

Examples 1 to 9

This series of examples demonstrates catalyst efficacy for the dehydrofluorination of 1,1-difluoroethane (HFC-152a) to vinyl fluoride (1141).

Table 1 (Examples 1 to 9) shows three specific catalysts, each studied in three different reactors: one to determine the rate of reaction, one for catalyst life, and one for coproduct formation.

TABLE 1

| Catalyst | First Reactor Example $k_f(\text{sec})^{-1}$ 275° C. | Second Reactor Example Hours (cat. life) 275° C. | Example % 1141 275° C. | Third Reactor Example % acetylene 260° C. |
|---|---|---|---|---|
| MgF$_2$ | 1 / 0.26 | 2 / 550 | 2 / 30 | 3 / 0.000 |
| MgF$_2$/AlF$_3$ (98:2) | 4 / 1.00 | 5 / 511 | 5 / 33 | 6 / 0.014 |
| MgF$_2$/AlF$_3$ (9:1) | 7 / 1.18 | 8 / 723 | 8 / 40 | 9 / 0.069 |
| CT(sec)-> | .055–.79 | 6 | 6 | 6 |

The reactor used to collect the data in Examples 1, 4, and 7 consisted of a 6" (15.2 cm)×¼" (0.64 cm) stainless steel tube. It was heated in a furnace to internal reactor temperatures of 225, 250, and 275° C. The rates of reaction were determined by measuring the percent conversion as a function of contact time; the actual flows of F152a were 10 ($1.7 \times 10^{-7}$ m$^3$/s), 25 ($4.2 \times 10^{-7}$ m$^3$/s), 38 ($6.3 \times 10^{-7}$ m$^3$/s), 50 ($8.3 \times 10^{-7}$ m$^3$/s), 75 ($1.3 \times 10^{-6}$ m$^3$/s), 100 ($1.7 \times 10^{-6}$ m$^3$/s), and 144 ($2.4 \times 10^{-6}$ m$^3$/s) sccm. The volume of catalyst used in all cases was 0.132 mL ground to 20–25 mesh (0.84–0.71 mm) and dried by heating at 250° C. for 1 hour while purging with dry nitrogen flowing at 25 sccm($4.2 \times 10^{-7}$ m$^3$/s). The rate of the dehydrofluorination was determined by fitting the data to the following set of equations,

$$CH_3CHF_2 \rightarrow CH_2=CHF + HF \qquad k_f$$

$$CH_2=CHF + HF \rightarrow CH_3CHF_2 \qquad k_r$$

while monitoring the HFC-152a and vinyl fluoride concentrations at the conditions mentioned above.

The data in Examples 2, 5 and 8 were determined in a ½" (1.3 cm)×11" (27.9 cm) tubular reactor made of Hastelloy™ nickel alloy. The catalysts were dried by heating to 350° C. for 16 hours under a flow of dry nitrogen of 50 sccm ($8.3 \times 10^{-7}$ m$^3$/s) prior to actual use. The reactor was cooled to 275° C. and a flow of F152a was begun at 50 sccm ($8.3 \times 10^{-7}$ m$^3$/s). When the flow of vinyl fluoride began to decrease from its near-equilibrium value, the run was concluded. All of the catalysts were ground to 12×20 mesh (1.68–0.84 mm).

The reactor used for the data in Examples 3, 6 and 9 was an Inconel™ nickel alloy ¾" (1.9 cm)×12" (30.5 cm) pipe with an internal diameter of ⅝" (1.6 cm). The catalysts (5 mL) were dried by heating to 260° C. under a flow of dry nitrogen of 50 sccm ($8.3 \times 10^{-7}$ m$^3$/s) prior to use. A flow of F152a was begun at 50 sccm ($8.3 \times 10^{-7}$ m$^3$/s). The reactor products were sampled every hour, and the products were determined by GCMS. All of the catalysts were ground to 12×20 mesh (1.68–0.84 mm).

Comparative Example A

Calcium fluoride (5.6 gm, 5.0 mL, 12–20 mesh (1.68–0.84 mm)) was placed in an Inconel™ nickel alloy ¾" (1.9 cm)×12" (30.5 cm) pipe with an internal diameter of ⅝" (1.6 cm). The catalyst was dried by heating to 250° C. under a flow of dry nitrogen of 50 sccm ($8.3 \times 10^{-7}$ m$^3$/s) prior to use. HFC-152a was passed into the reactor at 50 sccm ($8.3 \times 10^{-7}$ m$^3$/s) at 260 and 275° C. The results are shown in Table A.

TABLE A

| Temp(° C.) | % F152a | % 1141 |
|---|---|---|
| 260 | 99.5 | 0.5 |
| 275 | 99.8 | 0.8 |

Example 10

Magnesium oxide (5.4 gm, 5 cc, 12–20 mesh (1.68–0.84 mm)) was placed in an Inconel™ nickel alloy ¾" (1.9 cm)×12" (30.5 cm) pipe with an internal diameter of ⅝" (1.6 cm). The catalyst was dried by heating to 260° C. under a flow of dry nitrogen of 50 sccm ($8.3 \times 10^{-7}$ m$^3$s) prior to use, and activated by treating with a flow of HF up to 80 sccm ($1.3 \times 10^{-6}$ m$^3$/s) and up to 400° C. A flow of F152a was begun at 50 sccm ($8.3 \times 10^{-7}$ m$^3$/s). The contact time was 12 seconds. The reactor products were sampled every hour, and the products were determined by GCMS. The results are shown in Table 2.

TABLE 2

| Temp(° C.) | % F152a | % 1141 |
|---|---|---|
| 260 | 76.0 | 24.0 |

Example 11

ZnF$_2$ (1 mL, 12–20 mesh (1.68–0.84 mm)) was placed in a ¼" (0.64 cm)×3" (7.6 cm) tubular Hastelloy™ nickel alloy reactor. The reactor was heated to 275° C. and a flow of F152a was begun at 5 sccm ($1.7 \times 10^{-7}$ m$^3$/s) to give a contact time of 12 sec. The results are shown in Table 3.

TABLE 3

| Temp(° C.) | % F152a | % 1141 |
|---|---|---|
| 275 | 90 | 10 |

Example 12

ZnF$_2$/AlF$_3$ (9:1, 0.132 mL, 20–25 mesh (0.84 to 0.71 mm)) was placed in a 6" (15.2 cm)×¼" (0.64 cm) stainless steel tube heated in a furnace and was dried by heating at 250° C. for 1 hour while purging with dry nitrogen flowing at 25 sccm ($4.2 \times 10^{-7}$ m$^3$/s). The temperature was then raised to 275° C. and F152a was passed over the catalyst at 25 sccm ($4.2 \times 10^{-7}$ m$^3$/s). The contact time was 0.32 seconds. The conversion of F152a was monitored by gas chromatography; the %1141 was 15.

Comparative Examples B–H

The reactor was the same as that of Example 11 for Comparative Example B. ZnF$_2$/AlF$_3$ (1:9) (1 mL, 12–20 mesh (1.68–0.84 mm)) was heated to 275° C. and a flow of F152a was begun at 20 sccm ($1.7 \times 10^{-7}$ m$^3$/s) to give a contact time of 3 sec. The results are shown in Table B. For the rest of the comparative examples, the catalyst was placed in a 6" (15.2 cm)×¼" (0.64 cm) stainless steel tube heated in a furnace (0.132 mL, 20–25 mesh (0.84 to 0.71 mm)) and was dried by heating at 250° C. for 1 hour while purging with dry nitrogen flowing at 25 sccm ($4.2 \times 10^{-7}$ m$^3$/s). The temperature was then raised to 275° C. and F152a was passed over the catalyst at 25 sccm ($4.2 \times 10^{-7}$ m$^3$/s). The contact time was 0.32 seconds. The conversion of F152a was monitored by gas chromatography; the results are shown in Table B.

TABLE B

| Example | Catalyst | % 1141 |
|---|---|---|
| B | $ZnF_2/AlF_3$ (1:9) | 24 |
| C | $MgF_2/AlF_3$ (1:9) | 27 |
| D | gamma-$Al_2O_3$ | 28 |
| E | $ZnF_2/AlF_3$ (1:1) | 22 |
| F | $MgF_2/AlF_3$ (1:1) | 30 |
| G | alpha-$AlF_3$ | 22 |
| H | beta-$AlF_3$ | 12 |

What is claimed is:

1. A process for the manufacture of vinyl fluoride from 1,1-difluoroethane which comprises contacting said 1,1-difluoroethane at an elevated temperature with a catalyst containing at least one divalent Group II metal compound, characterized by:

contacting said 1,1-difluoroethane at a temperature of from about 200° C. to 400° C. with a catalyst containing (a) at least one compound selected from the oxides, fluorides and oxyfluorides of magnesium, zinc and mixtures of magnesium and zinc, and optionally (b) at least one compound selected from the oxides, fluorides and oxyfluorides of aluminum; provided that the atomic ratio of any metals other than magnesium and zinc, in total, to the total of magnesium and zinc in said catalyst is about 1:4, or less.

2. The process of claim 1 wherein a contact time is employed which is sufficient to provide a dehydrofluorination of 1,1-difluoroethane equal to at least 80% of the equilibrium value for conversion of 1,1-difluoroethane to vinyl fluoride at the temperature employed.

3. The process of claim 2 wherein the temperature is from 250° C. to 280° C.

4. The process of claim 3 wherein the catalyst consists essentially of magnesium fluoride.

5. The process of claim 3 wherein the catalyst consists essentially of magnesium fluoride and at least one compound selected from the oxides, fluorides and oxyfluorides of aluminum.

6. The process of claim 1 wherein the catalyst contains at least one compound selected from the oxides, fluorides, and oxyfluorides of aluminum.

7. The process of claim 6 wherein the atomic ratio of aluminum to the total of magnesium and zinc is about 1:9.

8. The process of claim 7 wherein the catalyst consists essentially of magnesium fluoride and at least one compound selected from the oxides, fluorides and oxyfluorides of aluminum.

9. The process of claim 1 wherein the catalyst consists essentially of magnesium fluoride.

10. The process of claim 1 wherein the catalyst consists essentially of magnesium fluoride and at least one compound selected from the oxides, fluorides and oxyfluorides of aluminum.

11. A processor the manufacture of vinyl fluoride from 1,1-difluoroethane which comprises contacting said 1,1-difluoroethane at an elevated temperature with a catalyst containing at least one divalent Group II metal compound, characterized by:

(1) said 1,1-difluoroethane being contacted with said catalyst at a temperature of from about 200° C. to 400° C.;

(2) said at least one divalent Group II metal compound being selected from the oxides, fluorides and oxyfluorides of magnesium; and (3) said catalyst further containing at least one compound selected from the oxides, fluorides and oxyfluorides of aluminum; provided that the atomic ratio of any metals other than magnesium, in total, to the total magnesium in said catalyst is about 1:4, or less.

12. The process of claim 11 wherein said catalyst consists essentially of magnesium fluoride and aluminum fluoride; and wherein said catalyst contact is sufficient to provide a dehydrofluorination of 1,1-difluoroethane to vinyl fluoride of at least 80% of the equilibrium value at the reaction temperature.

13. A process for the manufacture of vinyl fluoride from 1,1-difluoroethane which comprises contacting said 1,1-difluoroethane at an elevated temperature with a catalyst containing at least one divalent Group II metal compound, characterized by:

(1) said 1,1-difluoroethane being contacted with said catalyst at a temperature of from about 200° C. to 400° C.;

(2) said at least one divalent Group II metal compound being selected from the oxides, fluorides and oxyfluorides of magnesium; and (3) the atomic ratio of any metals other than magnesium, in total, to the total magnesium in said catalyst being about 1:4, or less.

14. The process of claim 13 wherein said catalyst consists essentially of magnesium fluoride; and wherein said catalyst contact is sufficient to provide a dehydrofluorination of 1,1-difluoroethane to vinyl fluoride of at least 80% of the equilibrium value at the reaction temperature.

* * * * *